United States Patent [19]

Shoesmith

[11] Plant 5,048

[45] May 3, 1983

[54] CHRYSANTHEMUM NAMED PINK CHIFFON (SP6-267-P)

[75] Inventor: Leonard H. Shoesmith, Westfield-Woking, England

[73] Assignee: Pan American Plant Company, Parrish, Fla.

[21] Appl. No.: 312,885

[22] Filed: Oct. 19, 1981

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new and distinct pink daisy chrysanthemum having a vigorous and rapid growth habit and a profuse production of relatively large blooms. This new plant is particularly suitable for year around production of cut flowers with a rapid eight-week response that is one week earlier than the "Marbles" and a good spray formation which does not compound as the "Marbles" does.

4 Drawing Figures

BACKGROUND OF THE NEW PLANT

This new daisy-type chrysanthemum was discovered by me in 1976 as a seedling of unknown parentage growing in a field of miscellaneous chrysanthemum plants cultivated in greenhouse at West Chicago, Ill., with the object of finding unusual and interesting varieties suitable for commercial production. This new plant was propagated at West Chicago, Ill., under my direction, by means of cuttings, and such propagation was carried through successive generations to determine the continuity of its distinctive features and its suitability for commercial scale propagation. Several years of propagation of this new plant, by cuttings at West Chicago, Ill., and at Cortez and Parrish, Fla., has demonstrated that its novel features hold true from generation to generation and appear to be firmly fixed.

DESCRIPTION OF THE DRAWINGS

This new type chrysanthemum is illustrated by the accompanying drawings, of which sheet one is a full color photographic view showing several stems of the new plant in full bloom illustrating the nature of the plant form and its blooms; sheet two is a photographic print of a close-up view of several flowers of this plant hand-painted to show their true coloration; sheet three is a machine print of a photocopy showing the top or front side of leaves of this new plant; and sheet four is a similar print showing the bottom or back side of the leaves shown in sheet three.

DESCRIPTION OF THE NEW PLANT

The following is a detailed description of my new pink chrysanthemum based upon observations of greenhouse grown plants made in the early Spring of 1981, the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Cut Mum.

Form: Perennial herbaceous bush of upright shape.

Height: Variable according to cultural treatment.
Growth: Vigorous, strong and upright.
Growth rate: Rapid.
Branching character: This plant branches well under normal conditions.
Foliage:
- *Quantity.*—Abundant.
- *Size of leaf.*—Up to about 110 mm. long and about 90 mm. wide.
- *Shape of leaf.*—Ovate with cleft margin.
- *Texture.*—Leathery.
- *Ribs and veins.*—Pinnate.
- *Color.*—Upper side — 139A. Under side — 137B.
- *Petioles.*—To about 30 mm. long.

THE BUD

Form: Globular.
Size: Variable in both diameter and length.
Opening rate: Typical chrysanthemum.
Color:
- *When phyllaries first divide.*—70C.
- *When petals begin to unfurl.*—74C.

Phyllaries:
- *Number.*—About 17.
- *Shape.*—Lanceolate.
- *Color.*—146D.

Flower stem:
- *Length.*—Variable.
- *Character.*—Rigid and erect.
- *Surface aspect.*—Pubescent.
- *Color.*—146D.

THE FLOWER

Blooming habit: Intermittent with profuse production of blooms.
Response: Eight weeks.
Blooms:
- *Size.*—Medium. Diameter — To about 90 mm. wide. Depth — Flat.

Borne: Cyme.
Form: A single daisy-type inflorescence borne on a receptacle surrounded by an involucre of bracts.
Shape:
- *When bloom first opens.*—Cup-shaped.
- *When bloom matures.*—Flat.

Petalage:
- *Phyllaries.*—About 19 in number.

*Florets.*—About 40 ray florets and many disc florets.

*Arrangement.*—Imbricated.

*Form.*—Lanceolate with rounded apex and entire margin.

*Texture.*—Soft.

*Aspect.*—Satiny.

*Color.*—Ray florets: Top side — 74C. Reverse side — 75B. Disc florets — Yellow.

Peduncle:

*Character.*—Strong and upright.

*Length.*—Varies.

*Color.*—146D.

Persistence of flower: Florets hang on and dry.

Fragrance: Typical chrysanthemum.

Lasting quality:

*On plant.*—3 to 4 weeks.

*As a cut flower.*—2 weeks.

REPRODUCTIVE ORGANS

Stamens:

*Number.*—Five.

*Arrangement.*—Syngenesious.

*Anthers.*—Size: Insignificant. Color: Yellow.

*Filaments.*—Length: Insignificant. Color: Yellow.

*Pollen.*—Color: Yellow.

Pistils:

*Number.*—One for each floret.

*Styles.*—Length: Insignificant. Color: Yellow.

*Stigmas.*—Color: Yellow.

Ovaries: Inferior bicarpellate.

This new and relatively large daisy chrysanthemum is particularly suitable for year around production in greenhouse for cut flowers. Its rapid response is a distinct advantage and, in general, this plant is considered an improvement over "Marbles".

I claim:

1. A new and distinctive pink daisy-type chrysanthemum, substantially as herein shown and described, particularly characterized by its rapid response, vigorous growth habit, and its profuse production of blooms.

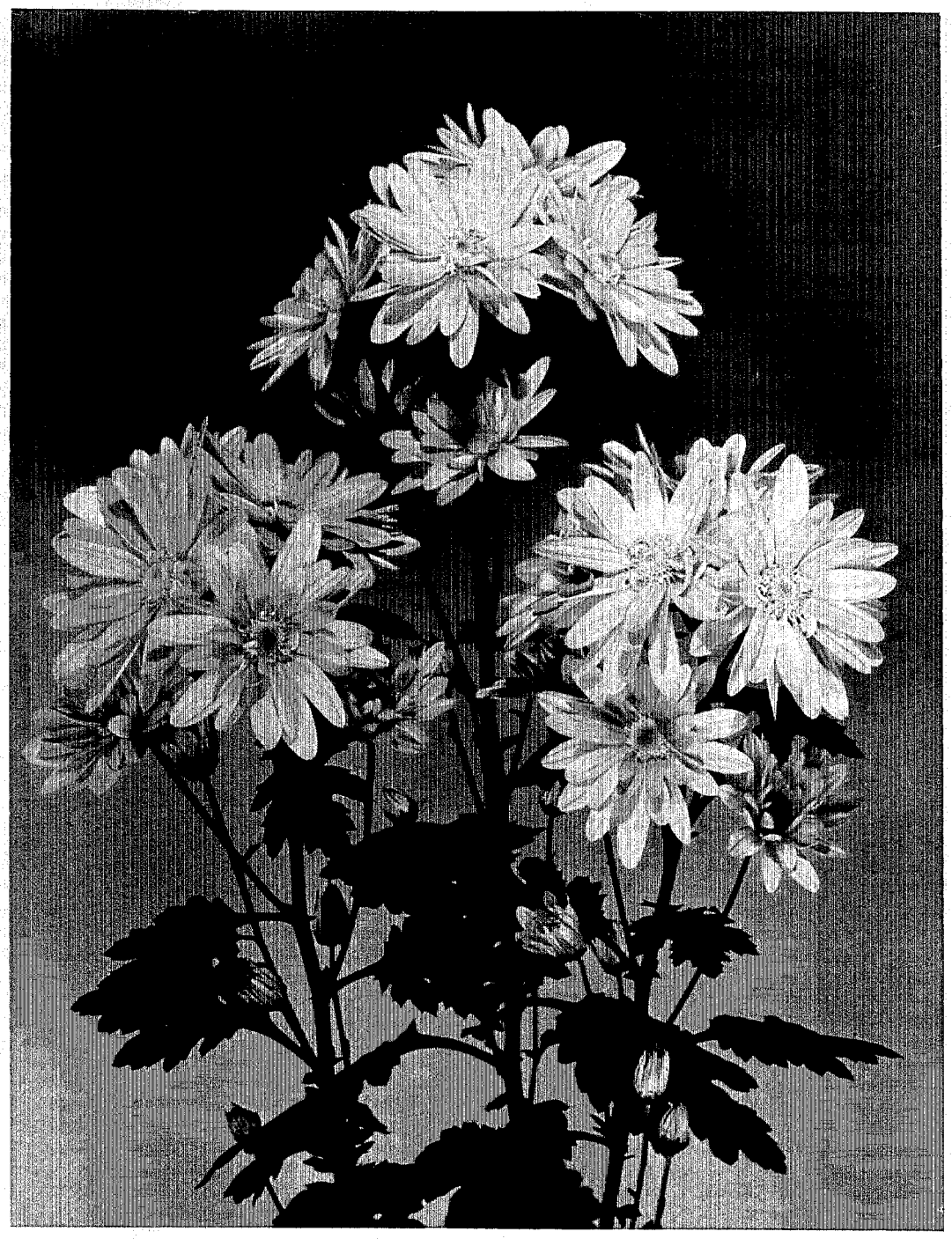

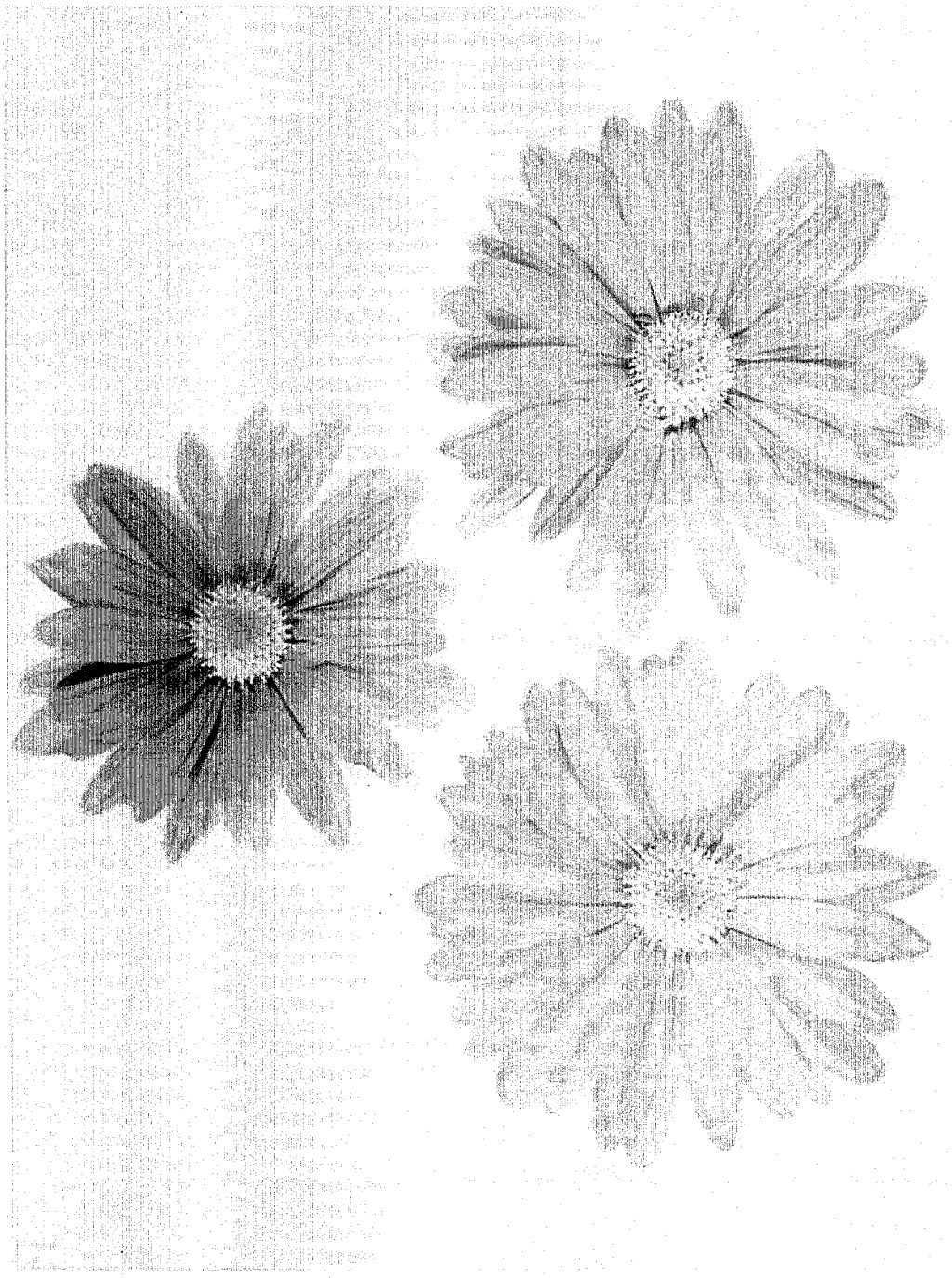

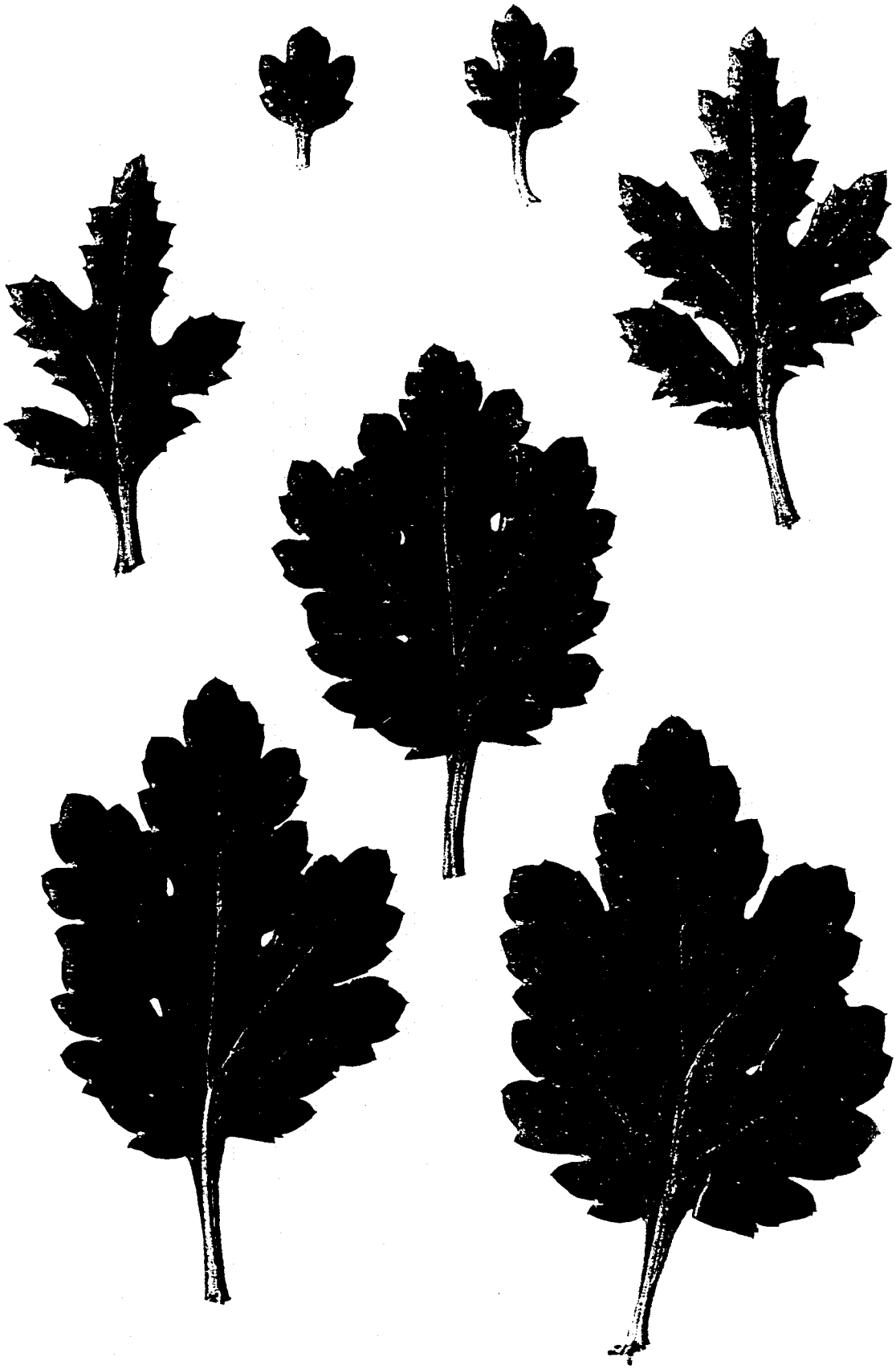

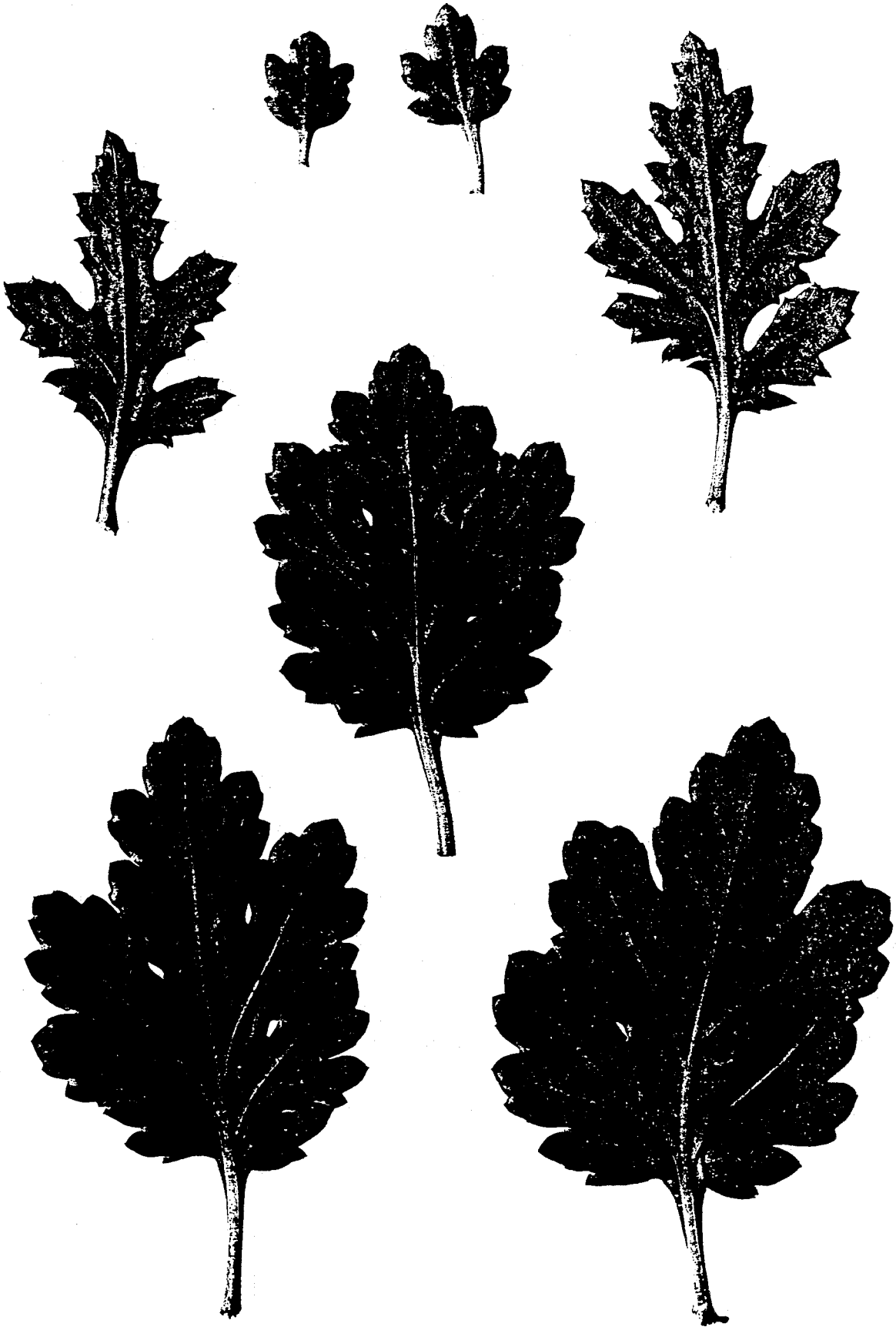

* * * * *